(12) United States Patent
Voronov et al.

(10) Patent No.: US 9,389,197 B2
(45) Date of Patent: Jul. 12, 2016

(54) BARRIER FILM DEFECT DETECTING METHOD AND APPARATUS

(71) Applicant: Samsung Display Co., Ltd., Yongin, Gyeonggi-Do (KR)

(72) Inventors: Alexander Voronov, Yongin (RU); Gyoo-Wan Han, Yongin (KR); Ji-Hun Jung, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 393 days.

(21) Appl. No.: 14/019,476

(22) Filed: Sep. 5, 2013

(65) Prior Publication Data
US 2014/0232419 A1    Aug. 21, 2014

(30) Foreign Application Priority Data

Feb. 18, 2013   (KR) .................... 10-2013-0016976

(51) Int. Cl.
| | | |
|---|---|---|
| *G01R 27/08* | (2006.01) | |
| *G01N 27/20* | (2006.01) | |
| *G01N 27/02* | (2006.01) | |
| *G01N 19/08* | (2006.01) | |
| *G01N 21/88* | (2006.01) | |
| *G01N 23/18* | (2006.01) | |

(52) U.S. Cl.
CPC .............. *G01N 27/20* (2013.01); *G01N 27/02* (2013.01); *G01N 19/08* (2013.01); *G01N 21/88* (2013.01); *G01N 23/18* (2013.01)

(58) Field of Classification Search
CPC ....... G01N 27/02; G01N 27/20; G01N 27/24; G01N 27/60; G01N 27/61; G01N 27/82; G01N 19/00; G01N 19/08; G01N 21/88; G01N 21/8851; G01N 21/892; G01N 21/896; G01N 21/9505; G01N 22/02; G01N 23/18; G01N 2203/006; G01N 2203/0062; G01N 2223/6466

USPC ......... 324/600, 649, 691, 693, 694, 500, 512, 324/541, 544, 555, 557, 713, 715, 718; 702/57, 58, 59, 127, 182, 183, 185
See application file for complete search history.

(56) References Cited

U.S. PATENT DOCUMENTS

| | | | | |
|---|---|---|---|---|
| 3,653,185 A * | 4/1972 | Scott | ........................ | B03C 3/38 110/119 |
| 4,492,981 A * | 1/1985 | Taketoshi | .............. | H01J 31/283 313/366 |
| 4,806,849 A * | 2/1989 | Kihira | ..................... | G01N 27/24 204/404 |
| 5,196,799 A | 3/1993 | Beard et al. | | |
| 5,969,532 A * | 10/1999 | Usui | ..................... | G01N 27/205 324/525 |
| 6,232,787 B1 | 5/2001 | Lo et al. | | |
| 6,663,791 B1 * | 12/2003 | Kawaguchi | ............ | G01B 15/02 216/61 |
| 2006/0152142 A1 * | 7/2006 | Nishitani | ................. | H01J 11/12 313/504 |
| 2009/0165536 A1 * | 7/2009 | Kinoshita | ........... | G01M 3/3272 73/52 |
| 2010/0266196 A1 | 10/2010 | Kasahara et al. | | |

FOREIGN PATENT DOCUMENTS

| | | |
|---|---|---|
| JP | 2009-164165 A | 7/2009 |
| KR | 10-2002-0087376 A | 11/2002 |

\* cited by examiner

*Primary Examiner* — Hoai-An D Nguyen

(74) *Attorney, Agent, or Firm* — Lewis Roca Rothgerber Christie LLP

(57) ABSTRACT

A method for detecting a defect of a barrier film includes preparing a device including an electrode and a barrier film covering the electrode, allowing a charged medium to contact a surface of the barrier film, and measuring a change in a flow of current between the charged medium and the electrode.

14 Claims, 4 Drawing Sheets

US 9,389,197 B2

BARRIER FILM DEFECT DETECTING METHOD AND APPARATUS

CROSS-REFERENCE TO RELATED APPLICATION

This application claims priority to and the benefit of Korean Patent Application No. 10-2013-0016976, filed on Feb. 18, 2013, in the Korean Intellectual Property Office, the disclosure of which is incorporated herein in its entirety by reference.

BACKGROUND

1. Field

One or more embodiments of the present invention relate to a method and apparatus for detecting a defect of a barrier film.

2. Description of the Related Art

A known method of measuring a moisture intrusion rate with respect to a barrier film is by using a calcium (Ca) electrode. When a Ca electrode is wrapped with a test barrier film and exposed in an environment of moisture and oxygen, the moisture and oxygen reacting with the Ca electrode may be detected by an optical or electrical measurement apparatus. In doing so, a special pad equipped with a Ca film is used, however, such a special pad may not be applied to a flat panel display device such as an organic light emitting diode (OLED) display. Also, because this measurement method is available only after moisture or oxygen has intruded into a barrier film due to a defect of the barrier film, it is not possible to detect existence of a defect using Ca electrodes before the intrusion of moisture or oxygen. When a display device is placed in a high moisture environment for long time due to this measurement, even if a barrier film is determined to have no defect, lifespan of the flat panel display device may be deteriorated.

U.S. Pat. No. 5,196,799 discloses that even a very small hole may be critical to a film intrusion rate.

SUMMARY

Aspects of the one or more embodiments of the present invention are directed toward a method and apparatus for measuring a defect of a barrier film coated on a surface of a flat panel display device that is mass-produced, in a non-destructive manner and/or during a manufacturing process within a very short time.

Additional aspects will be set forth in part in the description which follows and, in part, will be apparent from the description, or may be learned by practice of the presented embodiments.

According to one or more embodiments of the present invention, there is provided a method for detecting a defect of a barrier film includes preparing a device including an electrode and a barrier film covering the electrode, allowing a charged medium to contact a surface of the barrier film, and measuring a change in a flow of current between the charged medium and the electrode.

The charged medium may be a charged gas.

The method may further include allowing the charged gas to pass through a mesh of a conductive material and to contact the surface of the barrier film, in which the measuring of the change in the flow of current includes measuring a change in a flow of current between the mesh and the electrode.

The medium may be a liquid.

The liquid may be dimethoxyethane including ethylene glycol or LiF salt.

The medium may be a liquid metal.

The liquid metal may include indium and mercury.

According to one or more embodiments of the present invention, an apparatus configured to detect a defect of a barrier film includes a medium supply unit configured to supply a charged medium to a surface of the barrier film of a device including an electrode and the barrier film covering the electrode, and a measurement unit configured to measure a change in a flow of current between the charged medium and the electrode.

The medium supply unit may have a linear shape.

The medium supply unit may include a first medium supply unit extending along a first direction and a second medium supply unit arranged in a second direction perpendicular to the first direction.

The medium supply unit may include a conductive tip electrically coupled to a power source and arranged to face the surface of the barrier film, and a mesh provided between the conductive tip and the surface of the barrier film and electrically coupled to the measurement unit.

The medium supply unit may include a head including a core electrode that is electrically coupled to a power source and is configured to apply electricity to a liquid or a liquid metal, and to discharge the liquid or the liquid metal onto the surface of the barrier film, and a liquid supply unit coupled to the head and configured to provide the liquid or the liquid metal to the head.

The apparatus may further include an air lifting head that is coupled to the head and configured to discharge air between the head and the surface of the barrier film to restrict an amount of the liquid or the liquid metal on the surface of the barrier film.

The medium supply unit may include a roller configured to absorb a liquid or a liquid metal in a surface of the roller.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
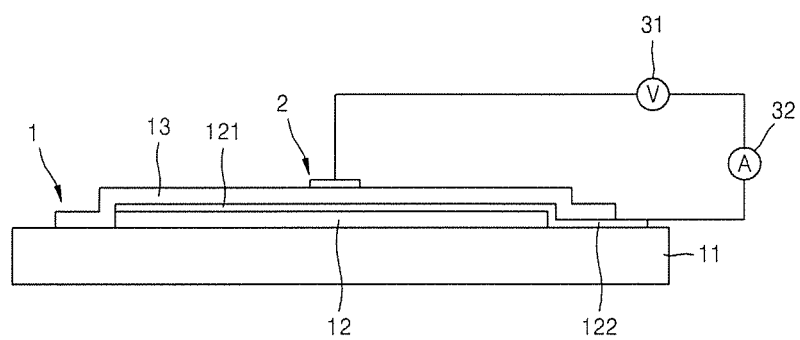
FIG. 1 is a schematic diagram illustrating a method of detecting a defect of a barrier film, according to an example embodiment of the present invention.

Reference will now be made in detail to embodiments, examples of which are illustrated in the accompanying drawings, in which, like reference numerals refer to the like elements throughout. In this regard, the present embodiments may have different forms and should not be construed as being limited to the descriptions set forth herein. Accordingly, the embodiments are merely described below, by referring to the figures, to explain embodiments of the present description. As used herein, the term "and/or" includes any and all combinations of one or more of the associated listed items. Expressions such as "at least one of," when preceding a list of elements, modify the entire list of elements and do not modify the individual elements of the list.

FIG. 1 is a schematic diagram illustrating a method of detecting a defect of a barrier film, according to an embodiment of the present invention. Referring to FIG. 1, first, a flat panel display device 1 is prepared. In the flat panel display device 1, a display portion 12 is formed on a substrate 11. A barrier film 13 hermetically seals the display portion 12 from external moisture and oxygen.

The flat panel display device 1 may be an organic light emitting display device. In this regard, the display portion 12 may be an organic light emitting display portion. However, the present invention is not only applied to the organic light emitting display device and, thus, any suitable device that benefits from being sealed off from external moisture and oxygen may be employed.

The display portion 12 includes a plurality of pixels and a common electrode 121 covers all pixels. The common electrode 121 may be a cathode electrode. The common electrode 121 is electrically coupled (or connected) to a conductive pad 122 outside the barrier film 13.

Figure 2:
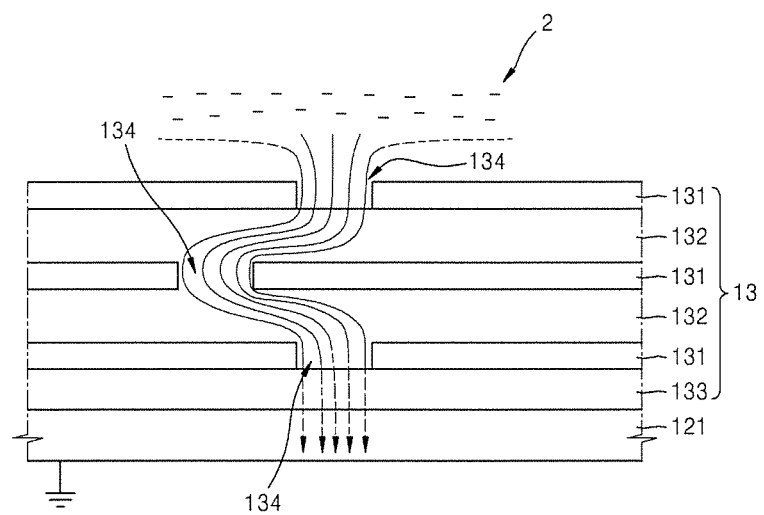
FIG. 2 is a schematic diagram illustrating the flow of charged particles in a barrier film.

The barrier film 13 may include at least one first film 131 and at least one second film 132, as illustrated in FIG. 2. The first film 131 includes an inorganic material and the second film 132 includes an organic material.

The inorganic material may include at least one of silicon oxide, silicon nitride, silicon oxynitride, aluminum oxide, aluminum nitride, aluminum oxynitride, tin oxide, phosphor oxide, boron phosphate, tin fluoride, niobium oxide, and tungsten oxide, however, the present invention is not limited thereto. The organic material may include acryl or polyimide, however, the present invention is not limited thereto.

The first film 131 and the second film 132 are alternatively formed. FIG. 2 illustrates that the first film 131 of three layers are formed and the second film 132 is interposed between the neighboring layers of the first film 131. However, the present invention is not limited thereto and the numbers of the first film 131 and the second film 132 may be changed.

A protective film 133 may be further provided between the lowermost layer of the first film 131 and the common electrode 121. The protective film 133 may prevent deposition damage to the common electrode 121 from occurring when the lowermost layer of the first film 131 is deposited. The protective film 133 may use a material such as LiF, lithium quinolate, $Alq_3$, etc.

One of the sensitive constituent elements of the flat panel display device 1 is a common electrode that is a cathode electrode. Because the cathode electrode is formed of an active metal having a low work function such as magnesium, aluminum, or calcium, it has high reactivity with moisture or oxygen. Thus, degradation of the cathode electrode may be one of the reasons for a dark spot defect.

The barrier film 13 is important not only for protection of an organic light emitting film of the display portion 12 but also for protection of the common electrode 121 that is the cathode electrode. However, according to a recent trend, the barrier film 13 is formed to be as thin as possible, as such, a barrier characteristic of the barrier film 13 may be degraded by even small particles. For example, as it may be seen from FIG. 2, a defect 134 may occur in the barrier film 13.

The defect 134 of the barrier film 13 may provide a path through which moisture or oxygen intrudes. However, it is difficult to detect intrusion of moisture or oxygen through the defect 134 of the barrier film 13. Because the detection of a flow of neutral molecules such as moisture or oxygen intruding into the barrier film 13 is difficult, a defect of the barrier film 13 is detected by using a flow of charged particles instead of a flow of moisture or oxygen. The charged particles may be ions or electrons. The ions or electrons may be injected into the barrier film 13 by utilizing a medium 2 that is an electrode contacting an outer surface of the flat panel display device 1, in particular, an outer surface of the barrier film 13. The medium 2 may be charged by being electrically coupled to a power source 31 as illustrated in FIG. 1. The medium 2 and the conductive pad 122 may be electrically coupled to a measurement unit 32. The measurement unit 32 may be a current measurement unit.

The flow of moisture or oxygen may be traced by a flow of charged particles (ions or electrons). The flow of charged particles may be accelerated by a strong electric field. In addition, the flow of charge particles may be more easily captured compared to the flow of neutral particles. Because the common electrode 121 is common to all pixels and is a final layer prior to the formation of the barrier film 13, the common electrode 121 may be used as an electrode for electrical measurement.

Thus, as it may be seen from FIGS. 1 and 2, after the medium 2 including charged particles, that is, the charged medium 2, is contacted to a surface of the barrier film 13, a change in a current flow between the charged medium 2 and the common electrode 121 is measured so that it may be detected whether there is a defect in the barrier film 13 or not.

When a voltage is applied across the barrier film 13 having the defect 134, insulation destruction of the barrier film 13, which is a dielectric film, may occur. Because an electric field is stronger in the vicinity of the defect 134, the insulation destruction may occur in the defect 134. Thus, the defect 134 may be detected not only by the current flow at a low voltage but also by the insulation destruction of a dielectric film.

Figure 3:
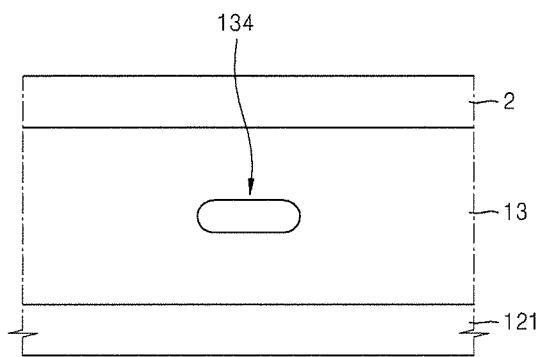
FIG. 3 is a schematic diagram for illustrating the insulation destruction of a barrier film.

FIG. 3 illustrates a case in which the defect 134 such as a void exists in the barrier film 13 that is a dielectric film. Referring to FIG. 3, when a voltage is applied between the common electrode 121 and the medium 2, an electric field in the defect 134 is higher than the electric field in other area of the barrier film 13. When energy of an ion in the defect 134 is sufficient to generate a second ionization process of distributing accelerated ions in surrounding neutral molecules, the process generates a natural jump (or increase) in the current flow. The existence of the defect 134 may be detected by detecting the jump of current.

When there is a defect in the dielectric film, insulation destruction may occur at a lower voltage as compared to a case in which no defect exists. Areas having a defect may experience destruction at a voltage remarkably lower than an insulation destruction voltage with respect to a film having no defect. Thus, whether a defect exists in the dielectric film 13 may be identified by measuring a range of a voltage at which insulation destruction occurs. In the present embodiment, the medium 2 may be a gas, a liquid, or a liquid metal.

Figure 4:
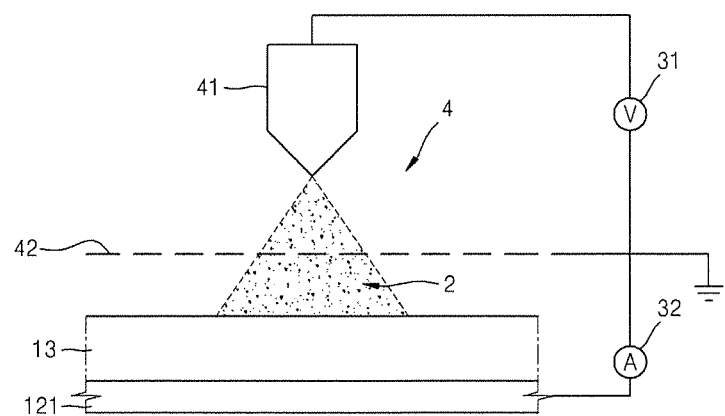
FIG. 4 is a schematic diagram illustrating an apparatus for detecting a defect of a barrier-film, according to an example embodiment of the present invention.

FIG. 4 is a schematic diagram illustrating an apparatus for detecting a defect of a barrier film, according to an embodiment of the present invention, in which a gas is used as the medium 2. Referring to FIG. 4, first, a medium supply unit 4 is located (or positioned) to face the barrier film 13. The medium supply unit 4 may include a conductive tip 41 and a mesh 42. The conductive tip 41 is located to face the barrier film 13 and may be electrically coupled to the power source 31. The mesh 42 is formed of a conductive material and is located (or positioned) between the conductive tip 41 and the barrier film 13. The mesh 42 and the common electrode 121 may be electrically coupled to the measurement unit 32, which according to this embodiment, is an ammeter.

When a high voltage is applied to the conductive tip 41 relative to the mesh 42, a high electric field is generated by the conductive tip 41 and thus ions are generated around neutral molecules of a gas located between the conductive tip 41 and the barrier film 13. The charged molecules accelerated by the applied electric field move toward the mesh 42. Parts of the charged molecules hit the mesh 42 and other parts of the charged molecules proceed toward a surface of the barrier film 13 so as to deposit a layer (or film) of the medium 2 formed by the charged gas on the surface of the barrier film 13. The medium 2 forms a surface electric potential on the surface of the barrier film 13.

Some current flows due to an electric potential difference between the surface of the barrier film 13 and the common electrode 121 so as to be detected by the measurement unit 32. If the barrier film 13 has a certain defect, the current may increase to be higher than that of other area of the barrier film 13 where no defect exists. Thus, the existence of a defect in the barrier film 13 may be detected.

An end of the conductive tip 41 for applying a voltage may be a sharp tip or one that injects a gas toward the barrier film 13. Any gas capable of generating ions and/or electrons by being charged as electrical voltage (power) is applied to the conductive tip 41 may be employed.

The medium 2 may be a liquid or a liquid metal. Any solution including salt may be used as the liquid. The conditions of salt and a solvent are as follows; the salt is inactive compared to other materials used for the common electrode, and the organic light emitting display device and the solvent is stable in a high electric field, and the solvent is removable from the surface of a barrier film.

For example, dimethoxyethane including a trace of LiF salt may be used. Although the dimethoxyethane is a dielectric liquid, the dimethoxyethane may become conductive by adding a trace of LiF. LiF salt may be a source of ions that penetrate a barrier film. Because LiF is included at a mere trace, LiF may not remain on the surface of the barrier film.

Ethylene glycol may be used as the above liquid because ethylene glycol has low conductivity and is a liquid that is inactive with magnesium and barrier film materials such as acryl polymer and amorphous aluminum oxide. Because ethylene glycol is a volatile liquid, ethylene glycol hardly remains on the surface of the barrier film 13 after being deposited on the surface of the barrier film 13.

A liquid metal may also be used as the medium 2. Most metals are in a solid state at room temperature except for some alkali metal, gallium metal, and mercury. For example, a Cs—K alloy, a K—Na alloy, a Ga—In—Sn alloy, a Ga—In—Sn—Zn alloy, a Ga—In alloy, Hg, Cs, Ga, etc. may be used as the medium 2. Among them, the Cs—K alloy and the K—Na alloy are very active with oxygen and moisture. Accordingly, to use these alloys, a sealed environment may be used. Use of mercury is restricted due to its toxicity. However, a mercury alloy including indium may be used.

Figure 5:
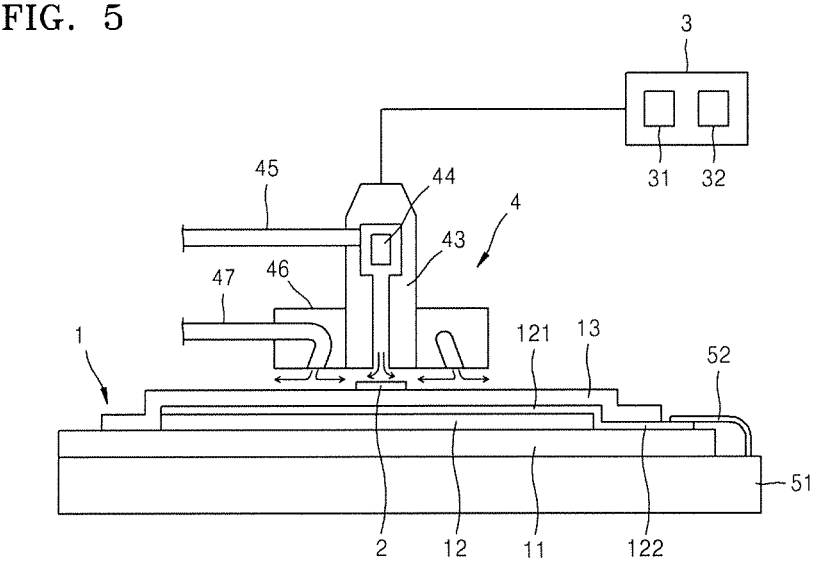
FIG. 5 is a schematic diagram illustrating an apparatus for detecting a defect of a barrier film, according to another example embodiment of the present invention.

FIG. 5 is a schematic diagram illustrating an apparatus for detecting a defect of a barrier film according to another embodiment of the present invention, in which the above-described liquid or liquid metal is used as the medium 2. Referring to FIG. 5, the medium supply unit 4 is arranged to face the barrier film 13. The medium supply unit 4 may include a head 43 and a liquid supply unit 45.

The liquid supply unit 45 is coupled to the head 43 and provides the head 43 with a liquid and/or a liquid metal that is used as the medium 2. The head 43 includes a core electrode 44 therein. The core electrode 44 is electrically coupled to the power source 31. The core electrode 44 charges the liquid and/or the liquid metal that is provided. The head 43 may be electrically coupled to a test unit 3 that includes the power source 31 and the measurement unit 32. A high resistance meter or a current-voltage test station may be used as the test unit 3.

An amount of the medium 2 that is charged and discharged onto the barrier film 13 through the head 43 may be limited by an air lifting head 46 on the surface of the barrier film 13. The air lifting head 46 is coupled to an air supply unit 47 and discharges air onto the surface of the barrier film 13. Accordingly, the amount of medium 2 may remain in a limited range. Also, a distance between the head 43 and the surface of the barrier film 13 may be maintained constant by the air lifting head 46.

In the apparatus for detecting a defect of a barrier film, according to the present embodiment, the flat panel display device 1 is placed on a table 51 that is grounded (or electrically grounded), and the conductive pad 122 is fixed by (or coupled to) a ground clip 52 so that the common electrode 121 may be grounded. In this state, a change in current flowing in the medium 2 is measured and thus whether a defect exists in the barrier film 13 may be determined.

Figure 6:
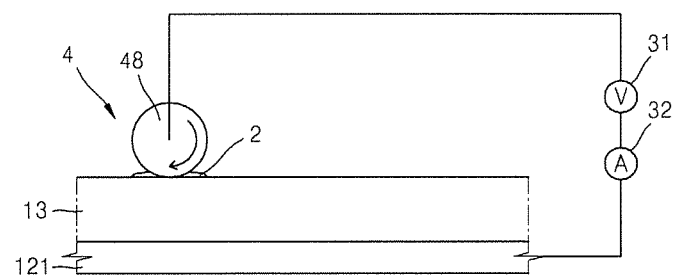
FIG. 6 is a schematic diagram illustrating an apparatus for detecting a defect of a barrier film, according to another example embodiment of the present invention.

FIG. 6 is a schematic diagram illustrating an apparatus for detecting a defect of a barrier film, according to another embodiment of the present invention, in which the above-described liquid or liquid metal is used as the medium 2. Referring to FIG. 6, the medium supply unit 4 may include a roller 48. A surface of the roller 48 may be formed of very soft conductive rubber sponge and the surface of the roller 48 may absorb the liquid or the liquid metal. The surface of the roller 48 may be electrically coupled to the power source 31.

The roller 48 may rotate in contact with the surface of the barrier film 13. Accordingly, the medium 2 adheres on the surfaces of the roller 48 and the barrier film 13. A change in the current due to an electric potential difference between the medium 2 and the common electrode 121 may be measured. Alternatively, a defect of the barrier film 13 may be detected by measuring a change in the current due to an electric potential difference between the surface of the roller 48 and the common electrode 121.

As described above, the apparatus for detecting a defect of a barrier film may identify a defect existing in a barrier film by scanning a surface of the barrier film. For convenience of scanning, the medium supply unit 4 may be formed to have a linear shape, e.g., as shown above. Accordingly, the existence of a defect in a barrier film may be detected by a one-time scanning process.

Figure 7:
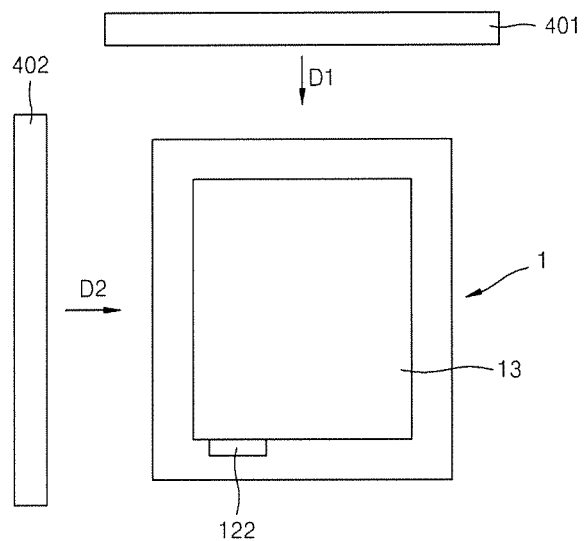
FIG. 7 is a schematic diagram illustrating an apparatus for detecting a defect of a barrier film, according to another example embodiment of the present invention.

To identify a two-dimensional location (or position) of a defect, the medium supply unit 4 may include a first medium supply unit 401 and a second medium supply unit 402 which are arranged perpendicular to each other, as illustrated in FIG. 7. The first medium supply unit 401 and the second medium supply unit 402 are each formed to have a linear shape and thus the number of scanning may be reduced. The X-Y coordinates of a defect existing in the barrier film 13 may be detected as the first medium supply unit 401 scans in a first direction D1 and the second medium supply unit 402 scans in a second direction D2.

As described above, according to the present invention, the existence and/or location of a defect of a barrier film may be detected by a simple method in a short time. As a result, there may not be a need to perform an aging process on a target test apparatus to detect a defect of a barrier film, and thus, the life span of the target test apparatus may not be affected at all. Also, the detection of a defect of a barrier film may be performed in any one operation (or stage) of a process of manufacturing the target test apparatus.

It should be understood that the example embodiments described herein should be considered in a descriptive sense only and not for purposes of limiting the scope of the invention. Descriptions of features or aspects within each embodiment should typically be considered as available for other similar features or aspects in other embodiments. It should be understood by those of ordinary skill in the art that various changes in form and details may be made to the example embodiments described above without departing from the spirit and scope of the present invention as defined by the following claims and equivalents thereof.

What is claimed is:

1. A method for detecting a defect of a barrier film of a display device, the method comprising:
    preparing the display device comprising:
        a substrate;
        a display portion on the substrate, the display portion being configured to emit light and comprising an electrode; and
        the barrier film sealing the display portion;
    allowing a charged medium to contact a surface of the barrier film; and
    measuring a change in a flow of current between the charged medium and the electrode.

2. The method of claim 1, wherein the charged medium is a charged gas.

3. The method of claim 2, further comprising allowing the charged gas to pass through a mesh of a conductive material and to contact the surface of the barrier film, wherein the measuring of the change in the flow of current comprises measuring a change in a flow of current between the mesh and the electrode.

4. The method of claim 1, wherein the medium is a liquid.

5. The method of claim 4, wherein the liquid is dimethoxyethane comprising ethylene glycol or LiF salt.

6. The method of claim 1, wherein the medium is a liquid metal.

7. The method of claim 6, wherein the liquid metal comprises indium and mercury.

8. An apparatus configured to detect a defect of a barrier film of a display device, the apparatus comprising:
    a medium supply unit configured to supply a charged medium to a surface of the barrier film of the display device comprising:
        a substrate;
        a display portion on the substrate, the display portion being configured to emit light and comprising an electrode; and
        the barrier film sealing the display portion; and
    a measurement unit configured to measure a change in a flow of current between the charged medium and the electrode.

9. The apparatus of claim 8, wherein the medium supply unit has a linear shape.

10. The apparatus of claim 9, wherein the medium supply unit comprises a first medium supply unit extending along a first direction and a second medium supply unit arranged in a second direction perpendicular to the first direction.

11. The apparatus of claim 8, wherein the medium supply unit comprises:
    a conductive tip electrically coupled to a power source and arranged to face the surface of the barrier film; and
    a mesh provided between the conductive tip and the surface of the barrier film and electrically coupled to the measurement unit.

12. The apparatus of claim 8, wherein the medium supply unit comprises:
    a head comprising a core electrode that is electrically coupled to a power source and is configured to apply electricity to a liquid or a liquid metal, and to discharge the liquid or the liquid metal onto the surface of the barrier film; and
    a liquid supply unit coupled to the head and configured to provide the liquid or the liquid metal to the head.

13. The apparatus of claim 12, further comprising an air lifting head that is coupled to the head and configured to discharge air between the head and the surface of the barrier film to restrict an amount of the liquid or the liquid metal on the surface of the barrier film.

14. The apparatus of claim 8, wherein the medium supply unit comprises a roller configured to absorb a liquid or a liquid metal in a surface of the roller.

* * * * *